United States Patent [19]

Gordon, Robert T.

[11] Patent Number: 4,996,991

[45] Date of Patent: * Mar. 5, 1991

[54] METHOD FOR FOLLOWING THE DISTRIBUTION OF PARTICLES IN NEUROLOGICAL OR NEUROMUSCULAR TISSUE AND CELLS

[76] Inventor: Gordon, Robert T., 4936 W. Estes, Skokie, Ill. 60077

[*] Notice: The portion of the term of this patent subsequent to Aug. 30, 2005 has been disclaimed.

[21] Appl. No.: 484,464

[22] Filed: Feb. 22, 1990

Related U.S. Application Data

[60] Continuation of Ser. No. 250,826, Sep. 27, 1988, abandoned, which is a division of Ser. No. 886,616, Jul. 18, 1986, Pat. No. 4,813,399.

[51] Int. Cl.$^5$ ................................................. A61B 5/00
[52] U.S. Cl. ............................... 128/653 R; 128/736; 600/10; 600/12; 424/9
[58] Field of Search .......................... 424/9; 600/9–10, 600/12; 128/653, 654, 736, 804

[56] References Cited

U.S. PATENT DOCUMENTS

| | | |
|---|---|---|
| 4,106,488 | 8/1978 | Gordon . |
| 4,136,683 | 1/1979 | Gordon . |
| 4,269,826 | 5/1981 | Zimmerman et al. ............... 424/101 |
| 4,303,636 | 12/1981 | Gordon ................................... 424/1 |
| 4,359,453 | 11/1982 | Gordon ................................... 424/1 |
| 4,545,368 | 10/1985 | Rand et al. . |
| 4,569,836 | 2/1986 | Gordon ................................. 424/1.1 |
| 4,574,782 | 3/1986 | Borrelli et al. . |
| 4,590,922 | 5/1986 | Gordon . |
| 4,622,952 | 11/1986 | Gordon . |
| 4,622,953 | 11/1986 | Gordon . |
| 4,662,359 | 5/1987 | Gordon . |
| 4,665,898 | 5/1987 | Costa et al. . |
| 4,735,796 | 4/1988 | Gordon ..................................... 424/9 |
| 4,767,611 | 8/1988 | Gordon ............................ 128/653 X |
| 4,813,399 | 3/1989 | Gordon ................................... 600/12 |

Primary Examiner—Ruth S. Smith
Attorney, Agent, or Firm—Banner, Birch, McKie & Beckett

[57] ABSTRACT

A process for following the exact distribution of particles in living neurological or neuromuscular tissue and cells. The process includes introducing particles into the tissue and cells, and thereafter measuring the alteration in dielectric properties, conductivity and frequency dependent dispersion curves of the tissue and cells.

1 Claim, 1 Drawing Sheet

METHOD FOR FOLLOWING THE DISTRIBUTION OF PARTICLES IN NEUROLOGICAL OR NEUROMUSCULAR TISSUE AND CELLS

This application is a continuation of application Ser. No. 07/250,826, filed Sept. 27, 1988, now abandoned which is a divisional of application Ser. No. 06/886,616, filed July 18, 1986, now U.S. Pat. No. 4,813,399.

INTRODUCTION

The treatment of neurological or neuromuscular disorders currently is limited to chemotherapy and various surgical approaches. The use of drugs is limited because of side-effects and the blood-brain barrier. Various drugs are used to affect neurotransmission to the extent that even neurotransmitters are used. The ability to control neurological or neuromuscular disorders with drugs is very limited and in many cases the mechanisms are not completely understood. In addition the ability to control the development and regeneration of nervous tissues as well as other tissues has not been achieved prior to this present invention.

BACKGROUND OF THE INVENTION

Diseases which affect the neurological system are multiple and consist of inflammatory lesions, conduction problems, and neurotransmission disorders. Different processes affect central nervous tissue vs. peripheral nervous tissue, myelinated nerve fibers vs. unmyelinated nerve fibers, and neurons themselves vs. glial cells and supporting cells. Most neurological diseases can only be very minimally treated because of the inaccessability of nervous tissue. Examples include amyotrophic lateral sclerosis, Alzheimer's disease, multiple sclerosis, Parkinson's disease, spinal cord problems i.e. diabetic neuropathy and retropathy, etc. Disorders of embryogenesis and development of neurological tissue as well as other tissues occur quite frequently and until the present invention there are very few methods of attempting to control this process. Developmental disorders are characterized by spinal cord malformations (i.e. spina-bifida, etc.) and cerebral malformations (hydrocephalous, etc.). Malignancies of the neurological system are also at present difficult to manage and extremely common in the developmental stages.

The present invention seeks to overcome this problem by modifying the intracellular environment in the neural and supporting cells to control the disease process.

OBJECT OF THE INVENTION

The present invention seeks to control the function of neurological tissue by the use of intracellular particles which are present, capable of being induced or introduced and the use of an alternating electromagnetic field to affect these particles and consequently the neurological tissue. Through the introduction of intracellular energy the function of the neuron as well as the conduction of the impulse can be controlled. A constant magnetic field can be used to impart a dipole to the particles prior to treatment with the alternating electromagnetic field to enhance the effect. In addition the constant magnetic field can be used to modify the behavior of the neural cells and to modulate the disease process or conduction mechanism.

DETAILED DESCRIPTION OF THE INVENTION

The use of particles to alter the energy level in the cell by the absorption of electromagnetic energy by the particle has been disclosed in the Applicant's U.S. Pat. Nos. 4,106,488; 4,136,683; 4,303,636; and 4,359,453. The present invention seeks to use particles to affect the absorption of energy by the cell itself and in particular by neural cells in the tissue. The implementation of this present treatment method in part utilizes inventive aspects which are the subject of other applications for U.S. Letters Patent by the same inventor as recited hereinafter. For example, a fuller understanding of the technology underlying the Gordon treatment reveals the operation of subtle mechanisms which can themselves become a contributing factor in the course of treatment and are incorporated herein by reference. The selection of particle compositions for use in this present invention as disclosed in the applicant's above described U.S. Patents No. and as disclosed in copending and commonly assigned applications, Ser. Nos. 418,298; 464,870 including continuation-in-part Ser. No. 522,941, including continuation-in-part Ser. No. 535,390, now U.S. Pat. No. 4,662,359, Ser. No. 524,844, now U.S. Pat. No. 4,590,922 and Ser. No. 561,811 as well as application Ser. No. 627,536 of the same inventor, are incorporated herein by reference.

Below several MHz the transmission of energy directly to the cell by an external alternating electromagnetic field is affected by the characteristics of the cell membrane. The charge accumulation on the membrane from intracellular and extracellular fluids accounts for the dielectric polarization of the membrane. The intracellular and extracellular electrolyte solution accounts for the conductance.

In the prior Gordon U.S. Pat. Nos. 4,303,636; 4,106,488; and 4,359,455, a high frequency magnetic field is employed to have a direct effect on the particles so that diseased cells can be killed by thermal effects due to hysteresis loss from the particles themselves when the field is relaxed. The particles of the present invention are utilized to alter the behavior of neuronal cells and supporting cells.

Through the introduction of particles in the nerve cells the intracellular conductivity can be altered as well as the charge accumulation on the cell membrane. The alteration in cell membrane characteristics enables the delivery of energy intracellularly at a lower frequency due to the effect of the charge accumulation on the cell membrane and the increased conductivity of the nerve cell allows more energy to be delivered and a better coupling at the given frequency.

Figure 1:
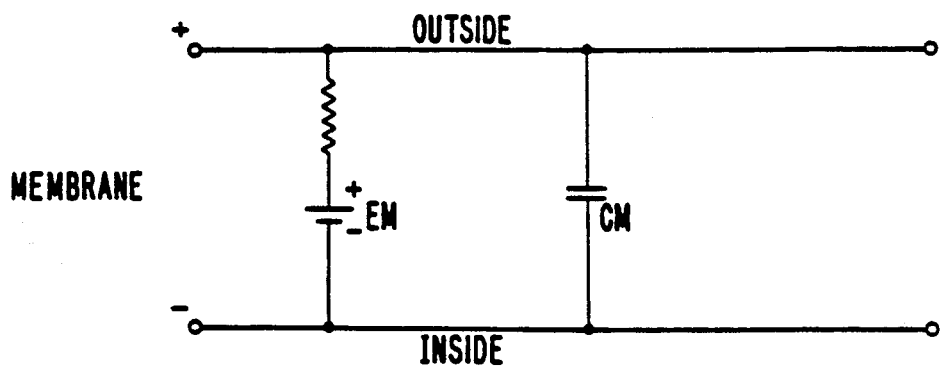

Mechanical, chemical, thermal stimuli as well as electrical can activate a nerve. Activation consists of initiation of an action potential with an alteration of ion permeability and the corresponding ion flexes. An analogous electrical circuit is described in FIG. 1. Obviously any change inside the cell will affect membrane polarization and conduction.

Figure 2:
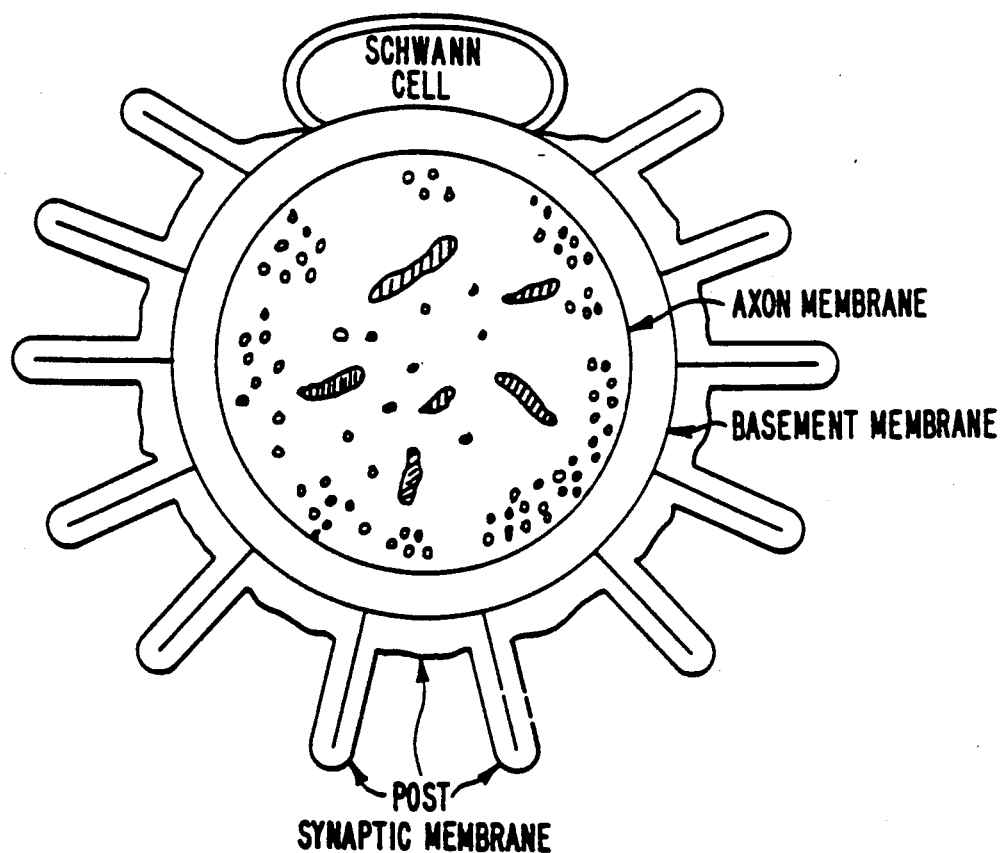

Synapses occur as connections between nerves and between nerves and other tissues. An example is the neuromuscular junction where the nerve ending is connected to the end plate of the muscle fiber. The nerve terminal is full of synaptic vesicles and mitochondria. This is illustrated in FIG. 2.

The neurotransmitters are often released at nerve endings or at synapses. Examples are acetylcholine or nor-epinephrine.

Iron is taken up quite well by certain areas of the brain. In certain pathological conditions increased or different accumulations of iron can occur. The blood brain barrier prevents the passage of most proteins into the brain. However the capillaries in the brain have demonstrated transferrin receptors for the uptake of iron. These are the only capillary receptors for transferrin in the body. Therefore iron uptake in the brain occurs by endocytosis via a receptor mediated mechanism. Iron is demonstrated in oligodendrocytes, glial cells and neurons. In addition active neurons have an inherent magnetic field secondary to their electric current. These magnetic fields can be monitored.

Neurons contain receptors. Transferrin receptors have been demonstrated on axons and dendrites. The ligand reaction with the receptor changes the membrane potential and ionic conductance which changes characteristics of nerves and causes transmitter release. An electric field can also affect transmitter release.

The uptake of iron in the brain can be modulated by chemical means. Chloroquin which is lysosomotropic can decrease the uptake by neuronal and glial cells. This uptake can also be decreased by ammonium chloride or methylamine. Iron accumulation in the brain is associated with neuromelanin, ceroid-lipofuscin and Hallervorden-Spatz syndrome.

The transport of iron particles and other particles in myelinated and unmyelinated fibers depends on the particle size and composition. Neurons take up iron particles by endocytosis. In unmyelinated nerves iron-dextran particles are transported along the unmyelinated pathways to the substantia nigra. After injection Fe-dextran is taken up by axons and transported retrograde to cell bodies. (No toxicity from iron particles in ganglion cell bodies of neuron).

Transport of the particles is extremely dependent on cell type and particle size, composition and conformation. In myelinated nerves iron-dextran is transported to the cell bodies in 2-3 weeks at a rate of 1-2 mm/day. However horse-radish peroxidase (HRP) is transported to the cell bodies in 20 hrs. at a rate of 2-3 mm/hour. Therefore different particles can be used to produce the effect in different areas. The iron dextran is longer than HRP and achieves cell body localization at a later time.

Most ganglia cells (cell bodies) will demonstrate iron after the axons are exposed to particles. In axons the iron dextran can cause swelling of myelin layers. The particles can embed in the myelin and react with it to decrease transport. However in the present invention the association of the particles with the myelin allows an affect to the myelin layers and the conduction in the axon. This is especially useful in diseases affecting the myelination of nerves.

Oligodendrocytes have endogenous iron and avidly take up Fe-dextran particles. This allows the ability to affect the function of the supporting glial cells as well.

Therefore the nerves do take up and transport iron particles. The present invention provides the ability to affect cells and metabolism in nerves and neurons. The particles can also be directed to the mitochondria of the axons and therefore affect the metabolic rate as well as the conduction of the nerves. The presence of these particles in the mitochondria at the nerve terminals in synapses or at neuromuscular junction allows for control of neurotransmitter release and also neuromuscular function.

Unmyelinated fibers label quickly with iron-dextran particles and travel via the nigrostriatal pathway to the thalamus and locus coeruleus pathway. This route can be used to affect central portions of the brain with the present invention.

Retinal ganglion cells can be labeled by injeciton into the superior colliculus and the lateral geniculate nucleus. This allows for control of the visual pathways. The dopaminergic neurons of the substantia nigra after striatal injection can also be controlled. Different pathways also transport the particles at a different rate.

In certain circumstances unmyelinated fibers as in the nigrostratatal system transport faster than the myelinated visual system. This can be due to the interaction of the particles with the myelin. This allows for control of one pathway over another depending on the timing and type of particle utilized. The transport of iron-dextran is affected by the interaction of the particles with the myelin and the uptake by the glial cells which decreases central transport. In thinly myelinated pathways as in the striatum-thalamus and thalamus-nucleus reticulous thalami paths the transport of iron particles is faster due to the decrease in interaction with the myelin. The fastest path for iron-dextran particles is the unmyelinated paths i.e. dopaminergic nigro striatal pathway and thalamus-locus coeruleus moradrenergic path.

The process of the present invention involves the use of intracellular particles to modify and modulate neuronal and glial cell function. These particles may be introduced into the subject by intravenous, intraarterial, intralymphatic injection or injection into the cerebrospinal fluid. The particles may also be injected directly into the neurological tissue or a specific pathway.

This process also applies to neurological tissue and other tissue during development to modify the developmental process. The expression of transferrin receptors for iron particles is extremely high during this phase.

The particles are of a ferromagnetic, paramagnetic, or diamagnetic nature and therefore capable of responding to an external alternating electromagnetic field. The particles, in general, are under 1 micron in size and in a colloidal-type suspension although for a direct injection they may be directly introduced.

In addition, any electric or magnetic dipole in the cell or capable of being induced in the cell may be utilized. A constant magnetic field can be used to induce these dipoles as well as enhance the effect of the external alternating electromagnetic field or dipoles or particles containing these dipoles which are present in the cell. This constant magnetic field can be used to help maximize particle uptake and absorption, and to help concentrate the particles in the desired area.

The choice of particle type, size and shape can be highly significant to effective treatment, particularly where subcellular localization or other subtle differentiations in metabolic activity, for example, are conveniently utilized to maximize particle uptake and absorption. Different particles are chosen depending on the desired pathway or ultimate area of nervous tissue which is desired to be affected as described above. Suitable particles and exemplifications of selection parameters are disclosed and examined in copending and commonly assigned application Ser. No. 535,390, now U.S. Pat. No. 4,662,359, of the same inventor, incorporated herein by reference.

The particle systems include metalloporphyrins, $Fe_2O_3$, metal-metalloporphyrins and particularly useful particle including both inorganic elements and compounds as well as metal containing organic compounds. Inorganic elements and compounds particularly well suited, owing to their favorable magnetic parameters, comprise elements such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal containing-organic molecules useful for the application described above, comprise particles of iron-dextrans such as FeOOH-dextran complexes and other dextran metal complexes wherein the metal is selected from the group comprising cobalt, iron, zinc, chromium, nickel, gallium, platinum, manganese and rare earth metals such as dysprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and dysprosium-gallium and iron such as $Fe_2O_3$ particles, $Fe_3O_4$ particles and FeOOH particles and $Fe_2O_3$-dextran complexes, $Fe_3O_4$-dextran complexes, and FeOOH-dextran complexes, and actinide series elements and compounds, ferric ammonium citrate, and various iron transporting and chelating compounds such as enterochelin, transferrin, etallothionein, hydroxamates, phenolates, ferrichromes, desferri-ferrichromes, ferritin, ferric mycobactins, and iron-sulfur proteins such as ferredoxin and rubredoxin and transferrin as well as transferrin compounds and complexes.

Particularly appropriate metal-containing organic structures for use with the present invention are the porphyrins such as etioporphyrins, mesoporphyrins, uroporphyrins, coproprophyrins, protoporphyrins, and dicarboxylic acid containing porphyrins and substituted porphyrins such as tetraphenylporphyrin sulfonate (TPPS). Especially advantageous protoporphyrins comprise hematoporphyrins, chlorophylls, and cytochromes. In addition to the naturally occuring protoporphyrins which possess either iron or magneium containing moieties, mixed-metal or di-metal hybrid porphyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, iron, manganese, zinc, chromium, gallium, nickel, platinum and rare earth series of metals such as dysprosium, erbium, europium, gadolinium holmium, samarium, terbium, thulium, ytterbium and ytterium, dimetallic compounds such as dysprosium-nickel, dysprosium-cobalt, gadolinium-iron, ytterbium-iron, cobalt-samarium, gadolinium-yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin such as protoporphyrins (e.g. hematoporphyrins) and the like.

The substitution reaction is carried out in vitro by reacting the desired metal with the desired porphyrin in the presence of the enzyme ferrochelatase (E.C. 4.11.1.1). Reaction conditions as described by Jones and Jones (Biochem. J. 113:507–, 1969) or Honeybourne, et al (FEBS Lett.: 98:207–10, 1979) are suitable.

Additional particle systems particularly suited to use in this present invention include $Fe_4O_4$-transferrin dextran, metal-transferrin (transition, rare-earth), metalloporphyrin-transferrin, antibody-ferritin-particles, antibody-ferritin-transferrin particles, antibody-transferrin particles, metal-porphyrin-metal complexes, metallothionein particles, and lectin particles. Useful particle systems for use in this present invention further comprise: Where particle=$Fe_3O_4$, transition metal, rare-earth metal, metalloporphyrin, etc. as well as ferromagnetic and paramagnetic particles.

One magnetic characteristic known to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp (K) | Mag. Sus. ($10^6$ cgs) |
| --- | --- | --- |
| Iron Oxide (ref.) | 293 | +7,200 |
| Dysprosium Oxide | 287.2 | +89,600 |
| Dysprosium Sulfate Octahydrate | 291.2 | +92,760 |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrates | 293 | +76,500 |
| Thulium | 291 | +25,500 |
| Thulium | 296.5 | +51,444 |
| Ytterbium Sulfide | 292 | +18,300 |

Thus, the enhanced magnetic characteristics displayed by the particles of the subject invention result in an increase in an electromagnetic field thereby increasing the overall sensitivity and control of the modalities for the improvement of the present invention techniques and for the resultant effects.

Magnetic susceptibility has also been used heretofore in connection with the treatment protocol as disclosed in U.S. Pat. No. 4,163,683 of the same inventor, where magnetic susceptibility measurements are correlated with temperature (an interdependent variable) in accomplishing the related induction heating step controllably. There is no recognition, however, that the values for magnetic susceptibility, independent of the induction heating step or the imposition of an electromagnetic field can be usefully correlated (to maximization of particle concentration with time to optimize treatment effectiveness, as demonstrated herein.

A further benefit is derived from the fact that some particle compositions comprise a ferromagnetic, paramagnetic, or diamagnetic component integrated into a cell or organelle specific molecular structure, thereby permitting efficient targeting and delivery of said particles to specific intracellular compartments such as mitochondria, chloroplast, nuclei, vacuoles, and the like.

In addition, particle systems which are kept outside the neural cells may be utilized to alter membrane events and affect the frequency of response and the energy transmission of the diseased neuronal cells. In certain circumstances these particles may be utilized to stabilize the membrane of normal neuronal cells and decrease their response to a field at a given frequency.

A steady magnetic or electric field may be used to enhance the uptake of particles by the neuronal cells as well as enhancing the membrane and cytoplasmic alterations which occur and are fully disclosed and described in copending and commonly assigned application Ser. No. 535,390, now U.S. Pat. No. 4,662,359, of the same inventor incorporated herein by reference. For example, the application of the localized static magnetic or electric field may occur concurrently with the application of an alternating, oscillating or pulsed electromagnetic field. That is to say, the localized static magnetic or electric field may be superimposed on the subject of interest while the alternating, oscillating or pulsed field is also being applied.

Temperature measurements are taken in living tissue of the host organism and correlating the temperature readings to the low frequency magnetic field causing alteration in dielectric properties and/or conductivity and/or frequency dependent dispersion curves. Once the temperature is correlated with these measurements, (dielectric properties, conductivity and frequency dependent dispersion curves) these measurements are then made along three axes at right angles to one another in the host organism from which a three dimensional temperature map of the body is produced by restructuring them in a three dimensional temperature model by computer processes well known in the art.

The frequency of the magnetic field is selected to enhance the dielectric properties, conductivity and electric dipoles of the neuronal cells and will vary depending upon the particles employed therein. The frequency, however, is adjusted so that thermal effects thereby obtained are not due to hysteresis loss from the particles themselves but rather the alteration in conductibility, dielectric properties and electric dipoles of the neuronal cells that are brought about by the use of the particles of the present invention. Generally, the range of frequencies that may be employed will be anywhere from about 1 Hz to about 500 MHz; 1 Hz to about 100 MHz; 1 Hz to less than 13 MHz; 1 Hz to about 100 KHz; 1 hertz up to less than 50 kilohertz and especially from about 10 hertz up to about less than 50 kilohertz as well as any frequency within these ranges or range of frequencies within the aforesaid ranges.

The present invention, therefore, will be practiced at the above frequencies and the copending applications incorporated herein by reference will give the person of ordinary skill in the art a disclosure of how to practice the present invention with the exception that the frequencies described above will be employed in lieu of those utilized in such copending applications.

To further illustrate the operation of this instant invention, the following treatment scenario is provided.

Reference herein to tissue, organ or cell population is intended in its most embracive and comprehensive sense, referring in general to the region of the host organism affected by the invasive abnormality, or the treatment region, as the context requires.

The subject receives an intravenous injection or direct injection of a colloidally suspended particle such as iron porphyrin (FeTPPS$_4$) at a dosage of 2–10 mg/kg. After a prescribed period of time which is dependent on the method of introduction of the particles i.e. after 24 hours—14 days after intravenous injection and 20 hours—10 days after direct injection, the subject is exposed to an alternating electromagnetic field at a frequency of 1 Hz to 100 MHz in this case 500 Hz for a period of approximately 10–20 minutes. The alternating electromagnetic field may be applied via a coil arrangement or via capacitor plates or via electrodes in the tissue or any suitable means available in the state of the art, and consistent in application to this present invention. The process may be repeated as is necessary.

This field supplies energy to the interior of the neuronal cells thereby affecting only the reactive and/or diseased neuronal cells and not the normal neuronal cells. The amount of energy can be precisely controlled to affect only the reactive and/or diseased neuronal cells and not the normal neuronal cells.

In summary, the introduction and absorption of minute particles into the neuronal cells alters the intracellular environment and the charge accumulation on the membrane. Consequently, lower power levels may be used to transmit energy into the neuronal cells. Lower frequencies may be used because of the alteration in membrane events and the effect on normal cells is greatly reduced because of the above as well as the state of the neuronal cell's membrane. In addition, modification can be performed by using particles to alter the extracellular environment as well. Ultrasound techniques are also enhanced.

In addition, since radio frequency fields can affect particles by causing reversible or irreversible changes in the particles, i.e. magnetostrictive induced vibrations, by affecting the particles with an alternating electromagnetic field in the range 1 Hz to 500 MHz either prior to or during treatment, the particles can be made more or less responsive to the field. This alternating field can produce acoustic changes in the particle and affect the neuronal cell and subcellular structures. Ultrasound can be used.

As disclosed by the applicant in his U.S. Pat. No. 4,136,683 and as disclosed in copending and commonly assigned application Ser. No. 535,390, now U.S. Pat. No. 4,662,359 (continuation-in-part to application Ser. No. 522,941) of the same inventor and incorporated herein by reference, this present invention can be used to create a three-dimensional temperature map of the body. In addition, the measurements of these properties in the manner described herein, allows one to follow the distribution of the particles in the body by following the change in the dielectric properties, conductivity, and frequency dispersion curves both before and after ingestion of the particles.

Molecules in a neuronal cell can be affected if $\mu B > kT$ (where $\mu$ is dipole moment, B is the field strength, k is the Boltzman constant, and T is absolute temperature). Consequently by introducing the particles and increasing the relative dipole moment in the neuronal cell the direct effects on molecules in the neuronal cell can be enhanced even beyond thermal effects. Therefore, this present invention may directly affect the molecules in the neuronal cell.

Through these processes the dielectric properties across the membrane can be affected including the stimulation and/or alteration of nerve impulses and/or electrical events.

The ionic environment around the surface of the particle by becoming polarized can produce increased dielectric properties as well. In addition, membrane effects with the anionic proteinaceious material which accumulates around the neuronal cell can produce local effects.

When you have a mixture with different dielectric properties relaxation phenomenon will occur not at a single frequency, but over a wide range of frequencies. The curve is broadened due to interactions in the mixture. Inclusion of material of low dielectric constant will lower the dielectric constant of the mixture. Therefore, the addition of particles to the inside of the neuronal cell broadens the frequency response of intracellular structures as compared to the other cells and structures. Particle geometry also affects the frequency response. Consequently, the presence of the particles allows for a differential affect on subcellular structures.

Through the use of magnetic susceptibility measurements as described in the applicant's U.S. Pat. No. 4,136,683 and as disclosed in copending and commonly assigned application Ser. No. 535,390, now U.S. Pat. No. 4,662,359 (continuation-in-part to application Ser. No. 522,941) and as disclosed in copending and commonly assigned application Ser. No. 627,536 of the same inventor and incorporated herein by reference, the uptake of particles in the neuronal cells and glial cells can be followed as a function of time. This may be used diagnostically to evaluate which neurons are affected by the disease process and by analyzing which cells take up the particles. The magnetic characteristics of the particle in the neuronal cell can be used to help diagnose which disease process is present in the neurological tissue. Magnetic mapping techniques can also be used.

The process of this present invention is further illustrated by the following examples:

EXAMPLE I

A colloidal solution of $Fe_3O_4$-dextran-transferrin is prepared in a concentration of 20 mg/cc in Rogers lactate. An intravenous injection of 2 cc is performed slowly over a period of 5 minutes. Over the next 48–72 hours, periodic measurements of magnetic susceptibility using a SQUID magnetometer as well as magnetic mapping measurements are performed. This allows identification of the neuronal cells which are involved, as well as helping to determine the type of disease process and the point in time of maximum uptake of the particles. At this time, the subject is subjected to the alternating electromagnetic field which destroys the reactive and/or inflammatory diseased cells in the tissue. Any diseased neurological tissue in the body can be treated by this process.

EXAMPLE II $FeTPPS_4$-Chloride 20 mg/cc is injected into the cerebrospinal fluid. After 36 hours localization is achieved in the neurons and the area to be treated is placed in a helical coil where an alternating electromagnetic field is applied. The field is applied for 3-4 minutes to achieve the alteration in cellular behavior and the disease process modified.

EXAMPLE III

A colloidal solution of $Fe_3O_4$-dextran-transferrin is prepared in a concentration of 20 mg/cc in Ringers lactate. 1 cc is injected stereotactically into the nigrostriatal pathway. After 24 hours localization is achieved in the thalamus. An alternating electromagnetic field is then applied to modulate thalamic function.

EXAMPLE IV

A colloidal solution of $Fe_3O_4$-dextran-transferrin is prepared at a concentration of 20 mg/cc and 1 cc is injected into a myelinated nerve. Interaction occurs between the particles and the myelin after 72 hours. An alternating electromagnetic field is then applied to affect the myelin of the nerve as well as the conduction system within the nerve.

What is claimed is:

1. A process for following the exact distribution of particles in living neurological or neuromuscular tissue and cells comprising:
   introducing particles into said tissue and cells, and
   thereafter, measuring the alteration in dielectric properties, conductivity and frequency dependent dispersion curves of said tissue and cells.

* * * * *